United States Patent
Petrash et al.

(10) Patent No.: US 6,692,840 B1
(45) Date of Patent: *Feb. 17, 2004

(54) POLYMER COATING FOR RUBBER ARTICLES

(75) Inventors: Stanislaw Petrash, Whippany, NJ (US); Chaodong Xiao, East Hanover, NJ (US); Apala Mukherjee, South Orange, NJ (US); Zhixin Li, Bridgewater, NJ (US); John S. Thomaides, Berkeley Heights, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/663,468

(22) Filed: Sep. 15, 2000

(51) Int. Cl.$^7$ .......................... B32B 25/04; B32B 25/12
(52) U.S. Cl. ..................... 428/492; 428/500; 428/36.8; 264/306
(58) Field of Search ................ 428/492, 500, 428/36.8; 264/306; 2/159, 161.7, 167, 168

(56) References Cited

U.S. PATENT DOCUMENTS

| | | |
|---|---|---|
| 4,070,713 A | 1/1978 | Stockum ........................ 2/168 |
| 4,143,109 A | 3/1979 | Stockum ...................... 264/112 |
| 4,310,928 A | 1/1982 | Joung ............................. 2/161 |
| 5,272,771 A | 12/1993 | Ansell et al. .................. 2/167 |
| 5,284,607 A | 2/1994 | Chen ............................ 264/37 |
| 5,395,666 A | 3/1995 | Brindle ....................... 428/36.4 |
| 5,405,666 A | 4/1995 | Brindle ....................... 428/36.4 |
| 5,543,218 A | 8/1996 | Bennett et al. .............. 428/375 |
| 5,691,069 A | 11/1997 | Lee ............................. 428/500 |
| 5,700,585 A | 12/1997 | Lee ............................. 428/500 |
| 5,712,346 A | 1/1998 | Lee ............................. 525/288 |
| 5,840,814 A * | 11/1998 | Majoros et al. ............. 525/502 |
| 5,881,386 A * | 3/1999 | Horwege et al. ............ 2/161.7 |
| 5,919,861 A * | 7/1999 | Kazmaier et al. ............. 525/26 |
| 5,948,861 A * | 9/1999 | Coolbaugh et al. ........... 525/88 |
| 5,959,041 A * | 9/1999 | Ruiz Santa Quiteria et al. .......... 525/332.9 |
| 5,993,923 A | 11/1999 | Lee ............................ 428/36.8 |
| 6,016,570 A * | 1/2000 | Vande Pol et al. ........... 2/161.7 |
| 6,150,468 A | 11/2000 | Schoenberg et al. ........ 525/222 |
| 6,150,488 A * | 11/2000 | Martin ........................ 528/34 |
| 6,153,706 A * | 11/2000 | Letchford et al. .......... 525/314 |
| 6,319,664 B1 * | 11/2001 | Bookbinder et al. ........... 435/4 |
| 6,347,408 B1 * | 2/2002 | Yeh ............................... 2/167 |
| 6,350,384 B1 * | 2/2002 | Dvornic et al. ............. 210/688 |

FOREIGN PATENT DOCUMENTS

EP     0 640 623 A2     7/1994     ............. C08C/1/15

OTHER PUBLICATIONS

Putlitz, B., Hentze, H., Landfester, K., and Antonietti, M., Langmuir, 16, 3214–3220, published on web Feb. 4, 2000.*
Web Article for "FoamStar", pp. 1–4, Cognis Coatings, unknown publication date.*
Poly. Sci. and Eng. Tech., J. Kennedy et al.: disclosure of U.S. patent 5,663,245.
Dictionary of Chemistry (Ed: D.Sharp, 5th edition, pp. 143, 381–382, 1990).
Kanaoka, S., Omura, T., Sawamoto, M, and Higashimura, T. (Macro., v. 25, 6407–6413, 1992).

* cited by examiner

*Primary Examiner*—Paul Thibodeau
*Assistant Examiner*—Kevin M. Bernatz
(74) *Attorney, Agent, or Firm*—Thomas F. Roland

(57) ABSTRACT

The present invention is directed to the use of a polymer coating composition having a dispersant, microbeads and a high Tg polymer with a Tg of greater than −10° C. for the inner coating on natural and synthetic rubber articles, particularly for latex gloves. The coating for rubber articles, provides an inner surface coating that reduces friction between the latex and the hand to allow convenient donning. They are deliverable from aqueous solution.

1 Claim, No Drawings

POLYMER COATING FOR RUBBER ARTICLES

The present invention relates to the use of a polymeric coating composition for rubber articles. In particular the polymeric coating composition is useful for the inside coating of latex gloves.

BACKGROUND OF THE INVENTION

As used herein, the terms latex glove or latex article refer to a glove or article made of natural or synthetic rubber. Conventional medical gloves made from natural or synthetic rubber are difficult to don without a lubricant. Generally, said gloves are manufactured with a powdered coating, such as corn starch, over the inner surface of the glove so that the gloves can be more easily put on. The powder coating is a known nuisance, as loose powder can become airborne. The powder tends to absorb proteins found in natural rubber latex and the powder is easily dislodged during donning and use, contaminating the surrounding environment and causing allergies and other negative effects. Further, the protein/powder complex serves as a food source for bacteria, allowing them to proliferate. Recently, there has been a growing demand for powder-free natural and synthetic rubber gloves, which do not use loose powder for donning and mold release.

Glove manufacturers have tried to find alternatives to using starch powder to coat gloves. Some latex glove manufacturers use a chlorination process to provide the slippage necessary to facilitate donning of the gloves. In this case, calcium carbonate is used as a mold release agent and washed away prior to chlorination. Although this reduces the tack and friction of the rubber, this process makes the rubber less pliant and reduces the shelf life of the glove.

Manufacturers have looked at polymer based coatings. To be an effective substitute for starch, the inner surface coating must not only reduce friction between the rubber and the hand to allow convenient donning, but also must allow the rubber to stretch without coating delamination, i.e. have a high coefficient of elongation combined with low tack and a low coefficient of friction. Further, the coating should be deliverable from an aqueous solution, which should be stable in extreme environmental conditions, and meet any relevant regulatory requirements.

Several types of coatings have been developed, primarily based on polyurethanes: U.S. Pat. No. 5,088,125 discloses gloves modified by an ionic polyurethane; U.S. Pat. No. 5,272,771 discloses gloves modified by an ionic polyurethane containing fully reacted isocyanate groups; and U.S. Pat. No. 5,534,350 discloses gloves in which the outer glove coating contains a polyurethane dispersion and the inside glove coating contains a polyurethane containing a silicone emulsion.

Other coatings which have been developed include emulsion copolymers, particularly core-shell, containing low surface energy monomers and hard monomers as disclosed in U.S. Pat. Nos. 5,691,069 and 5,700,585; or containing two monomers selected from styrene, methyl or butyl acrylates, methacrylic or acrylic acid and a silicone oligomer, with glass transition temperatures of less than 0° C. and from 0 to 100° C. respectively as disclosed in U.S. Pat. No. 5,712,346. These sequential emulsion polymerizations lead to substantially linear copolymers. Copending U.S. patent application Ser. No. 09/400,488 describes the use of star polymers as coatings for latex gloves.

Other coatings have been developed containing a slip conferring component: U.S. Pat. Nos. 4,070,713 and 4,143,109 disclose a medical glove with particulate matter securely embedded in, and randomly distributed throughout the inner layer; U.S. Pat. No. 5,395,666 discloses a flexible article coated with a binder and porous absorbent microparticles having average diameters of from 4 to about 20 microns and an oil adsorption greater than 180 g/100 g of powder.

Surprisingly, it has now been discovered that a formulation containing a high Tg polymer, a dispersant, and microspheres provides an excellent slip conferring coating to latex gloves and other natural and synthetic rubber articles. While a high Tg polymer alone can provide a good coating, it tends to precipitate, especially in the dilute solutions preferred in the glove industry. While not intending to be bound to any particular theory, it is believed that the addition of a dispersant to a composition containing a high Tg polymer and microspheres results in a stabilization of the high Tg polymer, and a stabilization and uniform dispersion of particles. The dispersant also assists in uniform or continuous film formation.

SUMMARY OF THE INVENTION

The present invention is directed to the use of a polymer coating composition having a dispersant, microspheres, and a high Tg polymer as a coating for rubber articles, particularly for the inner surface of latex gloves.

The dispersant serves to distribute the individual components within the coating composition. It can be polymeric or non-polymeric, preferably being a star polymer.

Microspheres are small beads having diameters below 60 microns. The microspheres decrease the area of contact with the rubber article, and thus reduce the friction.

The high Tg polymer is one having a Tg of from −10° C. to 120° C. The high Tg polymer acts as a friction-reducing agent and a binder.

Other embodiments of the invention are methods of making a glove in which a polymer coating composition having a dispersant, microspheres, and a high Tg polymer, is applied to the glove as the inner glove coating.

The coating is resistant to water and can be delivered from an aqueous solution.

DETAILED DESCRIPTION OF THE INVENTION

The present invention is directed to the use of a polymer coating composition having a dispersant, microspheres, and a high Tg polymer, as a coating for rubber articles, particularly for the inner coating of latex gloves.

Dispersants of the present invention promote the uniform distribution and stability of individual components within the polymer formulation. Preferably the dispersant is present at from 0.1 to 5% by weight, and most preferably from 0.5 to 3% by weight. The dispersant may be a polymer, a non-polymer, or a mixture thereof. Non-polymeric dispersants useful in the present invention include, but are not limited to, anionic, cationic, nonionic, and amphoteric surfactants.

Polymeric dispersants include both linear and star polymers. Linear polymers useful in the present invention include, but are not limited to, poly(vinyl alcohol); partially hydrolyzed poly(vinyl alcohol); poly(acrylic acid); poly (methacrylic acid); copolymers of acrylic acid and/or methacrylic acid with compatible ethylenically unsaturated monomers such as alkyl esters of (meth)acrylic acid, hydroxyalkyl esters of (meth)acrylic acid, alpha-methyl styrene, styrene, and derivatives thereof, vinyl acetate, crotonic acid, esters of crotonic acid, and acrylamide, and derivatives thereof. Other suitable linear polymeric dispersants include but are not limited to poly(maleic acid) and copolymers of maleic acid with compatible ethylenically unsaturated monomers such as mono- and diesters of maleic acid, (meth)acrylic acid, alkyl esters of (meth)acrylic acid, hydroxyalkyl esters of (meth)acrylic acid, alpha-methyl styrene, styrene, and derivatives thereof, vinyl acetate, crotonic acid, esters of crotonic acid, and acrylamide, and derivatives thereof. Other suitable linear polymeric dispersants include, but are not limited to, polystyrene sulfonates, which are typically obtained by sulfonating poly(styrene) or copolymers of styrene with compatible ethylenically unsaturated monomers including, but not limited to, (meth)acrylic acid, esters of (meth)acrylic acid, maleic acid, and mono- and diesters of maleic acid; condensates including but not limited to naphthalenesulfonic acid-formaldehyde condensate and melamine-formaldehyde condensate. Certain natural or naturally derived polymers useful in the present invention include but are not limited to tannins, lignins, lignosulfates, alginates, dispersed or soluble starches and modified starches, and cellulosic polymers.

Star or radial polymers, as used herein, is intended to describe polymers that have three or more polymeric arms emanating from a central core. These polymers can be prepared by various polymerization procedures such as anionic, cationic, and free radical mechanisms. The star polymers are usually formed by using either multifunctional initiators, multifunctional chain transfer agents, or multifunctional coupling agents. The star polymers have unique properties including: low viscosities in solution due to their compact structure and high melt viscosities due to extensive entanglements relative to their linear coatings.

Preferably, star polymers of the present invention comprise a polyvalent mercaptan core and three or more polymeric arms which extend radially from the core. The arms comprise homopolymers, random copolymers, or block copolymers. Further, arms within a single star structure may have the same or different composition.

Star polymers preferably used in the present invention are those described in U.S. patent application Ser. No. 09/400,488, incorporated by reference herein.

It is desirable that the polymer be deliverable from an aqueous solution, is stable at normal and elevated temperature, and meets regulatory requirements. Thus, a particularly suitable star copolymer will contain at least one hydrophilic monomer and at least one hydrophobic monomer. In order to be deliverable from an aqueous solution, the material must be sufficiently rich in hydrophilic monomer. Suitable hydrophilic monomers include those monomers that are ionic, e.g. anionic, cationic, or zwiterionic, or have sufficient nonionic polar functionality, e.g. hydroxyl or amido groups to render them hydrophilic. Optionally, a dispersant could also contain one or more low energy monomers, such as, for example, reactive silicones, copolymerizable silicones, fluorocarbons and fatty acid esters.

The polymeric dispersant may optionally include an adhesion promoter such as an olefinic monomer containing a imidazole or urea or carbamate functionality. Examples of such monomers include, but not limited to, 2-(2-Oxo-1-imidazolidinyl)ethyl methacrylate and 2-(2-Oxo-1-imidazolidinyl)ethyl methacrylamide. Additionally, the polymeric dispersant (or high Tg emulsion) may optionally include a small amount of an olefinic monomer containing crosslinkable functionality such as alcohols, acids, silanes, siloxanes, isocyanates and epoxides. Examples of such monomers include, but not limited to, vinyltriisopropoxysilane, vinyltrimethoxysilane, vintyltriethoxysilane, vinyl-tris(2-methoxy-ethoxy)silane and gamma-methacryloyloxypropyltrimethoxysilane.

The polymer coating composition contains microspheres. The microspheres are useful to reduce the friction between the coated rubber article, by decreasing the contact area with the coating. The microspheres have diameters below 60 microns, preferably from 5 to 40 microns, and most preferrably from 10 to 30 microns. The microsphere may be made of any material which is harder than the article being coated. Examples of microspheres useful in the present invention are those made of polyamides such as nylons, polymethylmethacrylate, polystyrene, polyethylene, polypropylene, polytetrafluoroethylene, polyesters, polyethers, polysulfones, polycarbonates, polyether ether ketones, and other thermoplastics and their copolymers, silica, and microcrystalline cellulose. Preferably the microspheres are present in the coating composition at from 0.01 to 1% by weight.

The high Tg polymer of the invention is a polymer or copolymer, which acts both as a binder and to reduce friction. A high Tg polymer in the context of the invention is one having a Tg from −10 to 120° C., preferably from 25 to 110° C. and most preferably from 40° C. to 70° C. Polymers useful in the present invention are those formed from ethylenically unsaturated monomers by means known in the art, or mixtures thereof. Particularly useful polymers include (meth)acrylic copolymers, vinyl acrylics, polyvinyl acetate, vinyl copolymers, ethylene-vinyl acetate copolymers, and polyurethanes. Optionally, a high Tg copolymer could also contain a low energy monomer, and adhesion promoter.

The high Tg polymer can be made by means known in the art. Preferably the polymer is formed by emulsion polymerization. It is preferably present in the coating composition at from 0.1 to 5% by weight.

In addition to the dispersant, microbeads and high Tg polymer, it can be advantageous to optionally add a rheology modifier to the coating composition. The rheology modifier is used to control the viscosity of the composition for ease of use in different manufacturing processes and equipment. Rheology modifiers useful in the present invention include, but are not limited to cellulosics such as hyroxyethylcellulose, cationic hydroxyethylcellulose, such as Polyquaternium-4 and Polyquaternium-10, hydrophobically modified hydroxyethylcellulose, carboxymethylcellulose, methylcellulose, and hydroxypropylcellulose; dispersed or soluble starches or modified starches; and polysaccharide gums such as xanthan gum, guar gum, cationic guar gum such as Guar Hydroxypropyltrimonium Chloride, and locust bean gum. Other suitable rheology modifiers include but are not limited to alkali swellable emulsion polymers, which are typically made by emulsion copolymerization of (meth)acrylic acid with compatible ethylenically unsaturated monomers such as alkyl esters of (meth)acrylic acid, hydroxyalkyl esters of (meth)acrylic acid, alpha-methyl styrene, styrene, and derivatives thereof, vinyl acetate, crotonic acid, esters of crotonic acid, and acrylamide, and derivatives thereof; hydrophobically modified alkali swellable emulsion polymers, which are alkali swellable emulsion polymers into which hydrophobic groups have been introduced; certain amphiphilic polyurethanes; poly(acrylamide), copolymers of acrylamide with compatible ethylenically unsaturated monomers, poly(vinyl amides) such as poly(vinyl pyrrolidinone); and copolymers of vinyl amides such as vinyl pyrrolidinone with compatible ethylenically unsaturated monomers. The rheology modifier is typically added at from 0.01 to 1% by weight, and preferably from 0.05 to 0.15% by weight, based on the polymer coating composition.

The polymer coating composition may also contain other additives known in the art, such as adhesion promoters, surfactants, crosslinking agents, biocides, low surface energy compounds, and fillers.

The polymer coating composition of the present invention is made by combining each of the ingredients to form an aqueous dispersion. For example the microspheres can be dispersed in the dispersant, and that mixture added to the rest of the composition.

The polymeric coating may be used to coat a variety of natural and synthetic rubber items, including gloves, prophylactics, catheters, balloons, tubing, and sheeting. A particularly suitable end use application is the coating of latex gloves, including surgeons' gloves, physicians' examining gloves, and workers' gloves, more particularly powder-free latex gloves. Such coating may be used on the inside of the glove to provide slippage and promote donning.

When used to coat gloves, the polymeric coating composition may be applied using standard methods known in the art. For example, one conventional method of making latex gloves is to dip a former or mold in the shape of a hand into a coagulant mixture containing calcium nitrate. After drying, the mold is immersed in a latex emulsion for a time sufficient for the rubber to coagulate and form a coating of the desired thickness. Optionally, the glove then may be water leached to remove rubber impurities. The formed glove is then oven cured and cooled. After cooling, the glove is stripped from the mold and inverted. To coat the inside of the glove, the polymer coating composition may be applied immediately before or after latex curing.

An adhesion promoter may be used, and for some polymers may be necessary, to add charge and increase the amount of polymer picked up. Such adhesion promoter is typically a water soluble salt such as sodium, calcium, zinc, or aluminum salts, particularly sodium chloride and calcium nitrate. The salt is typically provided in a concentration of up to about 40%, particularly from about 20 to about 40% by weight of coating suspension. The adhesion promoter is generally applied after leaching.

The latex article, i.e. glove, may be formed so that the polymer coating composition coats the inside surface of the article. The polymer coating composition provides the desired glove properties without the need for chlorination or other coatings, including powders. However, if only one surface is coated, chlorination or another coating may be used to provide the desired properties on the non-coated surface.

The following examples are presented to further illustrate and explain the present invention and should not be taken as limiting in any regard.

EXAMPLE 1

Preparation of a Heteroarm Star Copolymer

A mixture of 45 parts methyl methacrylate, 10 parts methacrylic acid, 6.5 parts pentaerythritol tetrakis (3-mercaptopropionate) and 100 parts isopropyl alcohol was placed in a four-necked 1 L round-bottomed flask equipped with a nitrogen inlet, condenser and thermometer. The reactor was heated to 75° C. while stirring under atmospheric nitrogen. 0.5 Parts 2,2'-azobisisobutyronitrile was added to the reaction vessel and it was heated at reflux for 45 minutes. Forty-five parts butyl acrylate was added to the reaction vessel and heating under reflux was continued for 2 hours. The reaction was cooled and 100 parts of 1.25% ammonium hydroxide was added and stirred for 30 minutes. The isopropyl alcohol was then removed and water was added to make a stable colloid. The final polymer was neutralized to a pH of 7.0 with a combination of ammonium hydroxide and acetic acid.

EXAMPLE 2

Preparation of Random Star Copolymer

A mixture of 45 parts methyl methacrylate, 10 parts methacrylic acid, 45 parts butyl acrylate, 6.5 parts pentaerythritol tetrakis (3-mercaptopropionate) and 100 parts isopropyl alcohol was placed in a four-necked 1 L round-bottomed flask equipped with a nitrogen inlet, condenser and thermometer. The reactor was heated to 75° C. while stirring under atmospheric nitrogen. 0.5 Parts 2,2'-azobisisobutyronitrile was added to the reaction vessel and it was heated under reflux for 2 hours. The reaction was cooled and 100 parts of 1.25% ammonium hydroxide was added and stirred for 30 minutes. The isopropyl alcohol was then removed and water was added to make a stable colloid. The final polymer was neutralized to a pH of 8.0 with ammonium hydroxide.

EXAMPLE 3

Preparation of Linear Copolymer

A mixture of 45 parts methyl methacrylate, 10 parts methacrylic acid, 45 parts butyl acrylate, 26 parts 1-dodecanethiol and 100 parts isopropyl alcohol was placed in a four-necked 1 L round-bottomed flask equipped with a nitrogen inlet, condenser and thermometer. The reactor was heated to 75° C. while stirring under atmospheric nitrogen. 0.5 Parts 2,2'azobisisobutyronitrile was added to the reaction vessel and it was heated under reflux for 2 hours. The reaction was cooled and 100 parts of 1.25% ammonium hydroxide was added and stirred for 30 minutes. After that the isopropyl alcohol was removed and water was added to make a stable colloid. The final polymer was neutralized to a pH of 8.0 with ammonium hydroxide.

EXAMPLE 4

Making a Polymer-coated Rubber Glove

A ceramic mold was cleaned from contaminants, rinsed, heated to 40 to 50° C. and immersed for 15 to 20 seconds into the coagulant, a 20% aqueous solution of calcium nitrate. After dipping into the coagulant, the coagulant-coated mold was partially dried. The mold with coagulant was then immersed into a natural rubber latex at room temperature for the time required to build up a latex deposit with a required thickness. The latex deposit was then briefly dried in the oven. The mold coated with above deposit was then leached in water at about 65° C. to remove natural rubber proteins. The leached latex deposit was then dried and dipped into a polymer coating composition for up to one minute. After dipping with polymer dispersion, the latex deposit was vulcanized in the oven by heating at 90 to 130° C. for 15 to 30 minutes. After vulcanization, the coated rubber article was cooled and stripped from the mold. The ceramic mold was then cleaned.

EXAMPLE 5

Making a Polymer-coated Rubber Glove

A ceramic mold was cleaned from contaminants, rinsed, heated to 40 to 50° C. and immersed for 15 to 20 seconds into the coagulant, a 20% aqueous solution of calcium nitrate. After dipping into the coagulant, the coagulant-coated mold was partially dried. The mold with coagulant was then immersed into a natural rubber latex at room temperature for the time required to build up a latex deposit with a required thickness. The latex deposit was then briefly dried in the oven. The mold coated with above deposit was then leached in water at about 65° C. to remove natural rubber proteins. The leached latex deposit was then vulcanized in the oven by heating at 90 to 130° C. for 15 to 30 minutes. After vulcanization, the coated rubber article was again leached in water, dried and dipped into a polymer coating composition for up to one minute. After drying the polymer lubrication layer, the glove was cooled and stripped from the mold. The ceramic mold was then cleaned.

EXAMPLE 6

Polymer Formulation (comparative)

The polymer coating composition was prepared containing 2.5% by weight of NACRYLIC 6408 (meth)acrylic emulsion from NACAN Products Limited, Tg of 52° C. The dispersion was not stable and lot of settling was observed at the bottom of the container shortly after mixing. The dispersion was unsuitable for coating rubber articles.

EXAMPLE 7

Polymer Formulation (comparative)

The polymer coating composition was prepared containing 30% by weight of NACRYLIC 6408 (meth)acrylic emulsion and 7.5% by weight of polymethylmethacrylate-co-ethylene glycol di-methacrylate copolymer beads having average diameter of 8 micron (ALDRICH 46,316–7). The dispersion was even less stable than in Example 6 and lot of settling was observed at the bottom of the container shortly after mixing. The dispersion was unsuitable for coating rubber articles.

EXAMPLE 8

Polymer Formulation (comparative)

The polymer coating composition was prepared containing 2.5% by weight of NACRYLIC 6408 (meth)acrylic emulsion, 0.25% by weight of polymethylmethacrylate-co-ethylene glycol di-methacrylate copolymer beads having average diameter of 8 micron (ALDRICH 46,316–7) and 0.075% by weight of KELTROL T xanthan gum. The dispersion was slightly more stable than in Example 6. This dispersion was used for coating rubber articles. A moderate improvement in frictional properties relative to the natural rubber was noticed, but the coating exhibited excessive cracking and peeling.

EXAMPLE 9

Polymer Formulation (comparative)

The polymer coating composition was prepared containing 1.5% of linear copolymer of Example 3, 1% by weight of NACRYLIC 6408 (meth)acrylic emulsion and 0.075% by weight of KELTROL T xanthan gum. The dispersion was significantly more stable than in Example 6 and slight settling was observed at the bottom of the container. The dispersion was used for coating rubber articles, which exhibited good donning properties.

EXAMPLE 10

Polymer Formulation (comparative)

The polymer coating composition was prepared containing 1.5% of heteroarm star copolymer of Example 1, 1% by weight of NACRYLIC 6408 (meth)acrylic emulsion and 0.075% by weight of KELTROL T xanthan gum. The dispersion was significantly more stable than in Example 5 and practically no settling was observed at the bottom of the container. The dispersion was used for coating rubber articles, which exhibited good donning properties.

EXAMPLE 11

Polymer Formulation (comparative)

The polymer coating composition was prepared containing 1.5% of random star copolymer of Example 2, 1% by weight of NACRYLIC 6408 (meth)acrylic emulsion and 0.075% by weight of KELTROL T xanthan gum. The dispersion was significantly more stable than in Example 6 and practically no settling was observed at the bottom of the container. The dispersion was used for coating rubber articles, which exhibited good donning properties.

EXAMPLE 12

Polymer Formulation (comparative)

The polymer coating composition was prepared containing 1.5% of heteroarm star copolymer of Example 1, 1% by weight of VINAMUL 3650, a vinyl acetate-vinyl chloride-ethylene-acrylate polymer having a Tg of 14° C.; and 0.075% by weight of KELTROL T xanthan gum. The dispersion was significantly more stable than in Example 6 and practically no settling was observed at the bottom of the container. The dispersion was used for coating rubber articles, which exhibited good donning properties.

EXAMPLE 13

Polymer Formulation

The polymer coating composition was prepared containing 1.5% of linear copolymer of Example 3, 1% by weight of NACRYLIC 6408 (meth)acrylic emulsion, 0.25% by weight of polymethylmethacrylate-co-ethylene glycol di-methacrylate copolymer beads having average diameter of 8 micron (ALDRICH 46,316–7) and 0.075% by weight of KELTROL T xanthan gum. The dispersion was significantly more stable than in Example 6 and slight settling was observed at the bottom of the container. The dispersion was used for coating rubber articles, which exhibited very good donning properties.

EXAMPLE 14

Polymer Formulation

The polymer coating composition was prepared containing 1.5% of linear copolymer of Example 3, 1% by weight of NACRYLIC 6408 (meth)acrylic emulsion, 0.25% by weight of ORGASOL 3502 DNAT nylon beads and 0.075% by weight of KELTROL T xanthan gum. The dispersion was significantly more stable than in Example 6 and slight settling was observed at the bottom of the container. The dispersion was used for coating rubber articles, which exhibited very good donning properties.

EXAMPLE 15

Polymer Formulation

The polymer coating composition was prepared containing 1.5% of heteroarm star copolymer of Example 1, 1% by weight of NACRYLIC 6408 (meth)acrylic emulsion, 0.25% by weight of polymethylmethacrylate-co-ethylene glycol di-methacrylate copolymer beads having average diameter of 8 micron (ALDRICH 46,316–7) and 0.075% by weight of KELTROL T xanthan gum. The dispersion was significantly more stable than in Example 6 and practically no settling was observed at the bottom of the container. The dispersion was used for coating rubber articles, which exhibited excellent donning properties.

EXAMPLE 16

Polymer Formulation

The polymer coating composition was prepared containing 1.5% of heteroarm star copolymer of Example 1, 1% by weight of NACRYLIC 6408 (meth)acrylic emulsion, 0.25% by weight of ORGASOL 3502 DNAT nylon beads and 0.075% by weight of KELTROL T xanthan gum. The dispersion was significantly more stable than in Example 6 and practically no settling was observed at the bottom of the container. The dispersion was used for coating rubber articles, which exhibited excellent donning properties.

EXAMPLE 17

Polymer Formulation

The polymer coating composition was prepared containing 1.5% of random star copolymer of Example 2, 1% by weight of NACRYLIC 6408 (meth)acrylic emulsion, 0.25% by weight of polymethylmethacrylate-co-ethylene glycol di-methacrylate copolymer beads having average diameter of 8 micron and oil adsorption of 55 mL/100 g (ALDRICH 46,316–7) and 0.075% by weight of KELTROL T xanthan gum. The dispersion was significantly more stable than in Example 6 and practically no settling was observed at the bottom of the container. The dispersion was used for coating rubber articles, which exhibited excellent donning properties.

EXAMPLE 18

Polymer Formulation

The polymer coating composition was prepared containing 1.5% of random star copolymer of Example 2, 1% by weight of NACRYLIC 6408 (meth)acrylic emulsion, 0.25% by weight of ORGASOL 3502 DNAT nylon beads and 0.075% by weight of KELTROL T xanthan gum. The dispersion was significantly more stable than in Example 6 and practically no settling was observed at the bottom of the container. The dispersion was used for coating rubber articles, which exhibited excellent donning properties.

EXAMPLE 19

Polymer Formulation

The polymer coating composition was prepared containing 1.5% of random star copolymer of Example 2, 1% by weight of NACRYLIC 6408 (meth)acrylic emulsion, 0.25% by weight of INEOS PMMA beads and 0.075% by weight of KELTROL T xanthan gum. The dispersion was significantly more stable than in Example 6 and practically no settling was observed at the bottom of the container. The dispersion was used for coating rubber articles, which exhibited excellent donning properties.

EXAMPLE 20

Polymer Formulation

The polymer coating composition was prepared containing 1.5% of random star copolymer of Example 2, 1% by weight of NACRYLIC 6408 (meth)acrylic emulsion and 0.25% by weight of polymethylmethacrylate-co-ethylene glycol di-methacrylate copolymer beads having average diameter of 8 micron and oil adsorption of 55 mL/100 g (ALDRICH 46,316–7). The dispersion was significantly more stable than in Example 6 and practically no settling was observed at the bottom of the container. The dispersion was used for coating rubber articles, which exhibited very good donning properties.

EXAMPLE 21

Polymer Formulation

The polymer coating composition was prepared containing 1.5% of linear copolymer of Example 3, 1% by weight of VINAMUL 3650, 0.25% by weight of polymethylmethacrylate-co-ethylene glycol di-methacrylate copolymer beads having average diameter of 8 micron (ALDRICH 46,316–7) and 0.075% by weight of KELTROL T xanthan gum. The dispersion was significantly more stable than in Example 6 and slight settling was observed at the bottom of the container. The dispersion was used for coating rubber articles, which exhibited very good donning properties.

What is claimed is:

1. A formed natural or synthetic rubber article having directly deposited thereon a single layer continuous film coating, said coating formed from an aqueous dispersion comprising:

(a) a polymeric dispersant comprising one or more heteroarm random star copolymers formed from at least one hydrophobic monomer and at least one hydrophilic monomer;

(b) 0.1 to 1 percent by weight, based on the coating composition, of microspheres having a diameter of less than 60 microns; and (c) 0.1 to 5 percent by weight, based on the coating composition, of a polymer having a Tg from 25° C. to 110° C.; and (d) 0.01 to 1 percent by weight based on the coating composition, of a rheology modifier.

* * * * *